United States Patent
Puig Montiel et al.

(10) Patent No.: US 8,114,439 B2
(45) Date of Patent: Feb. 14, 2012

(54) SYNTHETIC PEPTIDES REDUCING OR REMOVING BAGS FORMED UNDER THE LOWER EYE CONTOUR AND THEIR USE IN COSMETIC OR DERMOPHARMACEUTICAL COMPOSITIONS

(75) Inventors: Arturo Puig Montiel, Barcelona (ES); Juan Cebrían Puche, Barcelona (ES); Elena Passerini, E-Barcelona (ES)

(73) Assignee: Lipotec, S.A., Barcelona (ES)

( * ) Notice: Subject to any disclaimer, the term of this patent is extended or adjusted under 35 U.S.C. 154(b) by 500 days.

(21) Appl. No.: 11/664,574

(22) PCT Filed: Sep. 22, 2005
(Under 37 CFR 1.47)

(86) PCT No.: PCT/ES2005/000514
§ 371 (c)(1),
(2), (4) Date: Feb. 5, 2009

(87) PCT Pub. No.: WO2006/040374
PCT Pub. Date: Apr. 20, 2006

(65) Prior Publication Data
US 2010/0098769 A1 Apr. 22, 2010

(30) Foreign Application Priority Data
Oct. 5, 2004 (ES) .................................. 200402364

(51) Int. Cl.
*A61K 38/07* (2006.01)
*A61K 31/4178* (2006.01)
*A61K 9/50* (2006.01)
*A61K 9/127* (2006.01)
*C07K 5/10* (2006.01)

(52) U.S. Cl. ....... 424/490; 530/330; 424/450; 514/18.8; 514/397; 548/312.7

(58) Field of Classification Search .................. 514/18.8; 530/330; 548/312.7
See application file for complete search history.

(56) References Cited

U.S. PATENT DOCUMENTS
5,561,110 A * 10/1996 Michaelis et al. ............. 514/6.5

OTHER PUBLICATIONS

STN preliminary search_11664574_08062010.*
CAS_RN_820959-17-9_11664574 (2005).*
Base De Datos Registry. Chemical Abstracts Service. Columbus, Ohio. (EE.II.) recovered from STN International, Karlsrube (Alemania), (2005).
Rittes. "The Use of Phosphatidylcholine for Correction of Lower Lid Bulging Due to Prominent Fat Pads." *American Society for Dermatologic Surgery, Inc.* vol. 27. Apr. 2001. pp. 391-392.
Flynn et al. "Botulinum-A toxin Treatment of the Lower Eyelid Improves Infraorbital Rhytides and Widens the Eye." *American Society for Dermatologic Surgery, Inc.* vol. 27. Aug. 2001. pp. 703-708.

Albericio et al. "Preparation and Application of the 5-(4-(9-Fluorenylmethyloxycarbonyl)aminomethyl-3-,5-dimethoxyphenoxy)-valeric Acid (PAL) Handle for the Solid-Phase synthesis of C-Terminal Peptide Amides under Mild Conductions." *J. Org. Chem.* vol. 55. 1990. pp. 3730-3743.
Atherton et al. "Solid Phase Peptide Synthesis." *IRL Press at Oxford University*, 1989 pp. 1-61.
Bodanszky et al. "The Practice of Peptide Synthesis: $2^{nd}$ Edition." *Springer Lab Manual.* New York. 1984. pp. 77-126.
Barlos et al. "Veresterung von partiell geschützten peptid-fragmenten mit harzen. Einsatz von 2-chlortritylchlorid zur synthese von Leu15-gastrin I." *Tetrahedron Letters.* vol. 30. No. 30. 1989. pp. 3947-3950.—English Abstract provided.
Barlos et al. "Darstellung geschützter peptid-fragmente unter einsatz substituierter triphenylmethyl-harze." *Tetrahedron Letters.* vol. 30. No. 30. 1989. pp. 3943-3946.—English Abstract provided.
Castro et al. "Upper Lid Blepharoplasty." *Facial Plastic Surgery.* vol. 15. No. 3. 1999. pp. 173-181.
Greene et al. "Protective Groups in Organic Synthesis: $2^{nd}$ Edition." *John Wiley & Son.* New York. 1991. pp. 309-404.
Author Unknown. "IUPAC-IUB Joint Commission on Biochemical Nonmenclature (JCBN). Nonmenclature and Symbolism for Amino Acides and Peptides." *Eur. J. Biochem.* vol. 138. 1984. pp. 9-37.
Kaiser et al. "Color Test for Detection of Free Terminal Amino Groups in the Solid-Phase Synthesis of Peptides." *Anal. Biochem.* vol. 34 1969. pp. 595-598.
Kullmann. "Proteases as Catalysts for Enzymic Syntheses of Opioid Peptides." *J. of Biol. Chem.* vol. 255. No. 17. 1980. pp. 8234-8238.
Lloyd-Williams et al. "Chemical Approaches to the Synthesis of Peptides and proteins." *CRC Press*, New York, 1997. pp. 19-93.
Matsueda et al. "A p-Methylbenzhydrylamine Resin for Improved Solid-Phase Syntesis of Peptide Amides." *Peptides.* vol. 2. 1981. pp. 45-50.
Rink. "Solid-Phase Synthesis of Protected Peptide Fragments using a Trialkoxy-Diphenyl-Methylester Resin." *Tetrahedron Letters.* vol. 28. No. 33. 1987. pp. 3787-3790.
Stewart. "Solid Phase Peptide Synthesis. $2^{nd}$ Edition." *Pierce Chemical Company*, Illinois 1984. pp. 1-95.
Wang et al. "p-Alkoxybenzyle Alchohol Resin and p-Alkoxybenzyloxycarbonylhydrazide Resin for Solid Phase Synthesis of Protected Peptide fragments." *J. of Am. Chem. Soc.* vol. 95. vol. 4. 1973. pp. 1328-1333.

* cited by examiner

Primary Examiner — Yong Chu
(74) *Attorney, Agent, or Firm* — Merchant & Gould P.C.

(57) ABSTRACT

The invention relates to peptides of general formula (I):

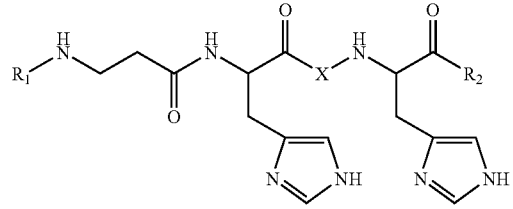

that can reduce or remove bags formed under the eyes, their stereoisomers and racemic or non-racemic mixtures thereof, and the cosmetically or dermopharmaceutically acceptable salts thereof, wherein X is cystenyl, seryl, threonyl or aminobutyryl; $R_1$ is H or alkyl, aryl, aralkyl or acyl group; and $R_2$ is amino, hydroxy or thiol, all of them substituted or non-substituted with aliphatic or cyclic groups. The invention also relates to a method of obtaining, cosmetic or dermopharmaceutical compositions containing them and their use for treating skin, preferably for reducing or removing bags formed under the eyes.

19 Claims, No Drawings

SYNTHETIC PEPTIDES REDUCING OR REMOVING BAGS FORMED UNDER THE LOWER EYE CONTOUR AND THEIR USE IN COSMETIC OR DERMOPHARMACEUTICAL COMPOSITIONS

CROSS REFERENCE TO RELATED APPLICATIONS

This application is the U.S. national stage application of PCT Patent Application No. PCT/ES2005/00514, Filed on Sep. 22, 2005, which claims the benefit of Spain Patent Application P200402364, filed on Oct. 5, 2004.

FIELD OF THE INVENTION

The present invention relates to synthetic peptides reducing or removing bags formed under the eyes and to cosmetic or dermopharmaceutical compositions containing said peptides useful in the treatment of skin, preferably facial skin, and especially the skin located under the eyes, with the aim of reducing or removing the swelling as well as improving its firmness, hydration and elasticity.

BACKGROUND OF THE INVENTION

The appearance of bags in the lower eye contour is a common cosmetic problem occurring when the skin of the lower eyelid is slightly swollen and hangs. The skin surrounding the eyes is relatively thin and has less oily composition than many other areas of the skin. For this reason, aging, stress, different illnesses and environmental pollution can show their first symptoms with a swelling of the lower eyelids and the appearance of bags due to the loss of firmness and elasticity of the skin which is located under the eyes. Fluid accumulation under the skin in the area located under the eyes gives rise to an edema which is shown as swollen eyes, frequently darker in comparison to surrounding facial areas ("dark circles"), which the consumer perceives as unacceptable or anti-aesthetic.

Up until now, the exact reasons for which anti-aesthetic under-eye bags are formed are not known, but different external factors such as stress, excessive caffeine or alcohol consumption and lack of sleep have been identified as associated factors or inducers of the problem. Likewise, the literature has described internal factors contributing to the formation of under-eye bags such as kidney malfunction and fluid retention, high blood pressure, inflammation, allergic components (allergic rhinitis) or lymphatic drainage alteration. Intrinsic skin aging, orbicular muscle relaxation as well as damage caused by ultraviolet radiation must also be considered together with these factors.

As the skin loses its elasticity and the muscles weaken with age, flaccid skin can accumulate around the eyes, forming folds in the eyelids. Furthermore, the fat accommodating and supporting the eyes in their sockets tends to move towards the outside of the eye cavities and to accumulate around the eyes in the form of bulging eyes. Swollen or bulging eyelids can be due to an accumulation of fat in the orbicular area as well as to an accumulation of flaccid skin of said area.

With the aim of recovering a young and a non-fatigued appearance of the facial expression, cosmetic surgery is frequently used to remove under-eye bags (blepharoplasty), in a process consisting of making internal and external incisions in the eyelids with the aim of removing the excess accumulated fat and/or skin. Blepharoplasty is currently the process that is most frequently carried out by plastic surgeons in the United States [Castro, E. and Foster, J. A. (1999) *Upper lid blepharoplasty Facial Plast. Surg.* 15 (3), 173-181]. However, despite the fact that said surgery is considered to be a minor surgical process, it is a technique that is not risk-free, due to the associated risks of the anesthesia used in the intervention as well as the risks of potential post-operative infections. Therefore, there is still a need to find a simple, effective and risk-free solution for reducing and removing under-eye bags.

DESCRIPTION OF THE INVENTION

The present invention provides a simple, effective and risk-free solution for reducing or removing the under-eye bags, comprising the development of synthetic peptides that can reduce or remove under-eye bags, as well as improve the firmness and elasticity of the skin of the lower eyelid area.

Therefore, a first aspect of this invention relates to a peptide that can reduce or remove bags formed under the eyes, according the general formula (I):

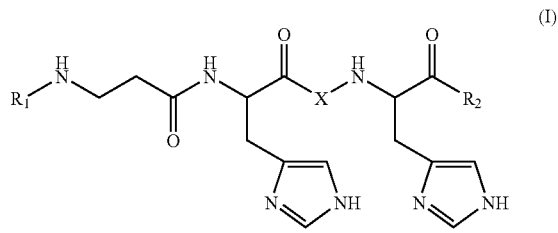

its stereoisomers and racemic or non-racemic mixtures thereof, and the cosmetically or dermopharmaceutically acceptable salts thereof, wherein:

X can be: cystenyl, seryl, threonyl or aminobutyryl;
$R_1$ can be: H or alkyl, aryl, aralkyl or acyl group; and
$R_2$ can be: amino, hydroxy or thiol, all of them substituted or non-substituted with aliphatic or cyclic groups.

The preferred structures of the peptides represented in the general formula (I) are those wherein:
X can be: seryl or aminobutyryl;
$R_1$ can be: H or saturated or unsaturated, branched or cyclic, linear $C_2$ to $C_{24}$ acyl; and
$R_2$ can be: amino or hydroxy, substituted or non-substituted with saturated or unsaturated, branched or cyclic, linear, aliphatic $C_1$ to $C_{24}$ groups.

The peptides of the present invention can exist as stereoisomers or mixtures of stereoisomers; for example, the amino acids forming them can have the L-, D-configuration or can be racemic independently of one another. It is therefore possible to obtain isomeric mixtures as well as racemates or diastereomeric mixtures, or pure diastereomers or enantiomers, depending on the number of asymmetric carbons and of which isomers or isomeric mixtures are present.

The preferred structures of the peptides of general formula (I) are pure isomers, i.e., enantiomers or diastereomers.

In the context of the present invention, the term "aliphatic group" relates to a saturated or unsaturated, linear or cyclic hydrocarbon group.

The term "hydrocarbon group" is used in the present invention to include alkyl, alkenyl and alkinyl groups for example.

The term "alkyl group" relates to a linear or branched, saturated hydrocarbon group, including for example, methyl, ethyl, isopropyl, isobutyl, t-butyl, heptyl, dodecyl, hexadecyl, octadecyl, amyl, 2-ethylhexyl, 2-methylbutyl, 5-methylhexyl and the like.

The term "alkenyl group" relates to a linear or branched, unsaturated hydrocarbon group, with one or more carbon-carbon double bonds, such as the vinyl group.

The term "group alkinyl" relates to a linear or branched, unsaturated hydrocarbon group, with one or more carbon-carbon triple bonds.

The term "cyclic group" relates to a closed hydrocarbon ring, which can be classified as alicyclic, aromatic or heterocyclic group.

The term "alicyclic group" relates to a cyclic hydrocarbon group with properties similar to aliphatic groups.

The term "aromatic group" or "aryl group" relates to a mono or polycyclic aromatic hydrocarbon group.

The term "heterocyclic group" relates to a closed hydrocarbon ring, in which one or more of the ring atoms is an element other than carbon (for example, nitrogen, oxygen, sulfur, etc.).

As understood in this technical area, the existence of high degree of substitution is not only tolerated but recommended. Therefore, there may be substitution in the peptides of the present invention. For the purpose of simplifying the present description of the invention, the terms "group" and "block" will be used to distinguish between chemical species allowing substitution or which can be substituted ("group"), and those not allowing substitution or which cannot be substituted ("block"). In this way, when the term "group" is used to describe a chemical substituent, the described chemical material includes both the non-substituted group and that containing O, N or S atoms.

On the other hand, when the term "block" is used to describe a chemical compound or substituent, only non-substituted chemical material can be included. For example, the expression "alkyl group" will not only include open-chain saturated alkyl substituents such as methyl, ethyl, propyl, isobutyl and the like, but also alkyl substituents containing other substituents known in the state of the art, such as hydroxy, alcoxy, amino, carboxyl, carboxamido, halogen atoms, cyano, nitro, alkylsulfonyl, and others. In this way, "alkyl group" includes ether, haloalkyl, alcohol, thiol, carboxyl, amine, hydroxyalkyl, sulfoalkyl, guanidine groups and others. On the other hand, the expression "alkyl block" is only limited to the inclusion of open-chain saturated alkyl substituents such as methyl, ethyl, propyl, isobutyl and the like.

The cosmetically or dermopharmaceutically acceptable salts of the peptides of formula (I) provided by this invention are included within the scope of the present invention. The term "cosmetically or dermopharmaceutically acceptable salts" includes the salts usually used to form metal salts or acid addition salts, either organic (such as acetate, citrate, oleate, oxalate or gluconate among others) or inorganic (such as for example chloride, sulfate, borate or carbonate among others). The nature of the salt is not critical, provided that it is cosmetically or dermopharmaceutically acceptable. The cosmetically or dermopharmaceutically acceptable salts of the peptides of formula (I) can be obtained by conventional methods, well known in the state of the art.

The synthesis of the peptides of general formula (I) can be carried out according to conventional methods known in the state of the art, such as for example the adaptation of solid-phase peptide synthesis methods [Stewart J. M. and Young J. D. (1984) *Solid Phase Peptide Synthesis, 2nd edition*, Pierce Chemical Company, Rockford, Ill. Bodanzsky M. and Bodanzsky A. (1984) *The practice of Peptide Synthesis*, Springer Verlag, New York. Lloyd-Williams, P., Albericio, F. and Giralt, E. (1997) *Chemical Approaches to the Synthesis of Peptides and Proteins*. CRC, Boca Raton (Fla., USA)], solution synthesis, a combination of solid-phase synthesis and solution synthesis methods or enzymic methods [Kullmann W (1980) *Proteases as catalysts for enzymic syntheses of opioid peptides J. Biol. Chem.* 255, 8234-8238]. The peptides can also be obtained by the fermentation of a bacterial strain that is modified or unmodified by genetic engineering with the aim of producing the desired sequences.

For example, a method for obtaining peptides of general formula (I) is that in which a fragment of the peptide of general formula (I), having a free carboxyl group or a reactive derivative thereof, is reacted with a complementary fragment, having an amino group, with at least one free hydrogen atom, with the subsequent formation of an amide type bond, and wherein the functional groups of said fragments that do not participate in the formation of the amide-type bond, if they exist, are conveniently protected with temporary or permanent protective groups.

Another example of a method for obtaining of peptides of general formula (I) is that in which a fragment of the peptide of general formula (I) having a leaving group, such as for example the tosyl group, the mesyl group and halogen groups among others, is reacted with a complementary fragment having an amino group with at least one free hydrogen atom by means of a nucleophilic substitution reaction, and wherein said functional groups of the fragments that do not participate in the formation of the N—C bond, if they exist, are conveniently protected with temporary or permanent protective groups. Examples of protective groups, their introduction and elimination are described in the literature [Greene T. W. (1981) *Protective groups in organic synthesis*, John Wiley & Sons, New York. Atherton B. and Sheppard R. C. (1989) *Solid Phase Peptide Synthesis: A practical approach*, IRL Oxford University Pres]. The term "protective groups" also includes polymeric supports used in solid-phase synthesis.

When the synthesis is carried out completely or partially in solid phase, the following can be mentioned as solid supports to be used in the method of the invention: supports made of polystyrene, polyethylene glycol-grafted polystyrene and the like, such as for example p-methylbenzhydrylamine resins (MBNA) [Matsueda G. R. and Stewart J. M. (1981) *A p-methylbenzhydrylamine resin for improved solid-phase synthesis of peptide amides Peptides* 2, 45-50.], 2-chlorotrityl resins [(a) Barlos K., Gatos D., Kallitsis J., Papaphotiu G., Sotiriu P., Wenqing Y. and Schäfer W (1989) *Darstellung geschützter peptid-fragmente unter einsatz substituierter triphenylmethylharze Tetrahedron Lett.* 30, 3943-3946. (b) Barlos K., Gatos D., Kapolos S., Papaphotiu G., Schäfer W. and Wenqing Y. (1989) *Veresterung von partiell geschützten peptid-fragmenten mit harzen. Einsatz von 2-chlortritylchlorid zur synthese von Leu15-gastrin I Tetrahedron Lett.* 30, 3947-3951], TentaGel® resins and the like, which may or may not include a labile spacer such as 5-(4-aminomethyl-3,5-dimethoxyphenoxy) valeric acid (PAL) [Albericio F., Kneib-Cordonier N., Biancalana S., Gera L., Masada R. I., Hudson D. and Barany G. (1990) *Preparation and application of the 5-(4-(9-fluorenylmethyloxycarbonyl)aminomethyl-3,5-dimethoxyphenoxy)-valeric acid (PAL) handle for the solid-phase synthesis of C-terminal peptide amides under mild conditions J. Org. Chem.* 55, 3730-3743], 2-[4-aminomethyl-(2,4-dimethoxyphenyl)phenoxyacetic acid (AM) [Rink H. (1987) *Solid-phase synthesis of protected peptide fragments using a trialkoxy-diphenyl-methylester resin Tetrahedron Lett.* 28, 3787-3790], Wang [Wang, S. S. (1973) *p-Alkoxybenzyl Alcohol Resin and p-Alkoxybenzyloxycarbonylhydrazide Resin for Solid Phase Synthesis of Protected Peptide Fragments J.*

*Am. Chem. Soc.* 95, 1328-1333] and the like, allowing the deprotection and simultaneous cleavage of the compound from the polymeric support.

The peptides according to the invention can form part of several types of compositions for their external application in a body of a mammal, preferably a human being. In this sense, the invention provides a cosmetic or dermopharmaceutical composition comprising peptides of general formula (I). Said compositions can be prepared by conventional methods known by persons skilled in the art.

The peptides object of the invention have a variable water-solubility, according to the nature of the $R_1$, $R_2$, and X groups. Those which are not water-soluble can be solubilized in conventional cosmetically or dermopharmaceutically acceptable solvents such as for example ethanol, propanol or isopropanol, propylene glycol, glycerin, butylenes glycol or polyethylene glycol. The peptides can also be previously incorporated in cosmetic carriers such as liposomes, milliparticles, microparticles and nanoparticles as well as in sponges, millispheres, microspheres and nanospheres, millicapsules, microcapsules and nanocapsules.

These preparations can be used in different types of formulations such as for example, creams, lotions, gels, oils, liniments, serums, mousses, ointments, bars, pencils or sprays, including "leave on" and "rinse-off" formulations, and can also be incorporated by means of techniques known by persons skilled in the art to different types of solid accessories such as towelettes, hydrogels, adhesive (or non-adhesive) patches or face masks, or can be incorporated to different make-up line products such as concealers, make-up foundations, lotions, make-up removal lotions among others.

The compositions mentioned in the present invention can contain additional ingredients commonly used in compositions for the care and treatment of skin, such as for example and in a non-limiting sense, emulsion agents, emollients, organic solvents, skin conditioners such as for example, humectants, alpha hydroxy acids, moisturizers, vitamins, pigments or dyes, gelling polymers, thickeners, softeners, anti-wrinkle agents, whitening agents, compounds capturing free radicals, anti-oxidizing compounds, compounds stimulating the synthesis of dermal or epidermal macromolecules and/or able to prevent their degradation, such as for example compounds stimulating collagen synthesis, compounds stimulating elastin synthesis, compounds inhibiting collagen degradation, compounds stimulating fibroblast proliferation, compounds stimulating keratinocyte proliferation, compounds stimulating keratinocyte differentiation, skin relaxing compounds, compounds stimulating glycosaminoglycan synthesis, firming compounds, compounds acting on capillary circulation, compounds acting on cell metabolism, compounds stimulating melanin synthesis, preservatives, perfumes, chelating agents, plant extracts, essential oils, marine extracts, cell extracts and sunscreens (organic or mineral photoprotection agents that are active against ultraviolet A and B rays), among others, provided that they are physically and chemically compatible with the rest of the components of the composition and especially with the peptides of the present invention.

The compositions of the present invention can contain or be coadministered with analgesic compounds and/or anti-inflammatory compounds for the purpose of reducing the swelling and irritation associated to under-eye bags. Steroid type compounds such as hydrocortisone or natural extracts or essential oils with intrinsic anti-inflammatory and analgesic activity can be emphasized among these compounds.

The peptides of general formula (I) are used in the cosmetic or dermopharmaceutical compositions of the present invention at cosmetically or dermopharmaceutically effective concentrations to achieve the desired effect; preferably between 0.00001% (by weight) and 10% (by weight); preferably between 0.0001% (by weight) and 5% (by weight) and more specifically between 0.001% (by weight) and 1% (by weight).

Therefore, an additional aspect of this invention relates to the use of peptides of general formula (I) in the manufacture of a cosmetic or dermopharmaceutical composition for the treatment of skin, preferably facial skin and more specifically for reducing or removing under-eye bags.

The present invention further provides a cosmetic or dermopharmaceutical method for reducing or removing bags formed under the eyes in humans, comprising the administration of an effective amount of peptides of general formula (I), preferably in the form of a cosmetic or dermopharmaceutical composition containing it.

EXAMPLES

The following specific examples provided herein are useful for illustrating the nature of the present invention. These examples are included solely for illustrative purposes and must not be interpreted as limitations to the invention claimed herein.

General Methodology

Chemical Synthesis

All the synthetic processes are carries out in polypropylene syringes equipped with porous polyethylene disks. All the reagents and solvents are of a quality for synthesis and are used without any additional treatment. The elimination of the Fmoc group is carried out with piperidine-DMF (2:8, v/v) (1×1 minutes, 1×5 minutes; 5 mL/g resin) [Lloyd-Williams, P., Albericio, F. and Giralt, E. (1997) *Chemical Approaches to the Synthesis of Peptides and Proteins*. CRC, Boca Raton (Fla., USA)]. The washings between the steps of deprotection, coupling and, once again, deprotection have been carried out with DMF (3×1 minutes) using 10 mL of solvent/g of resin each time. The coupling reactions have been carried out with 3 mL of solvent/g of resin. The control of the couplings is carried out by means of the ninhydrin test [Kaiser, E., Colescott R. L., Bossinger C. D. and Cook P. I. (1970) *Color test for detection of free terminal amino groups in the solid-phase synthesis of peptides Anal. Biochem.* 34, 595-598]. All the synthetic transformations and washings have been carried out at 25° C.

The chromatographic analysis by HPLC was carried out in Shimadzu equipment (Kyoto, Japan) using a reversed-phase column thermostatted at 30° C. (250×4.0 mm, Kromasil $C_8$, 5 µm, Akzo Nobel, Sweden). The elution was carried by means of a gradient of acetonitrile (+0.07% TFA) in water (+0.1% TFA) at a flow of 1 mL/minutes and the detection is carried out at 220 nm.

Abbreviations

The abbreviations used for the amino acids follow the rules of the IUPAC-IUB Commission on Biochemical Nomenclature specified in *Eur. J. Biochem.* (1984) 138, 9-37 and in *J. Biol. Chem.* (1989) 264, 633-673.

Abu, 2-aminobutyric acid; βAla, beta-alanine, 3-aminopropionic acid; AM, 2-[4-aminomethyl-(2,4-dimethoxyphenyl)-phenoxyacetic acid; Boc, tert-butyloxycarbonyl; DCM, dichloromethane; DIEA, N,N-diisopropylethylamine; DIPCDI, N,N'-diisopropylcarbodiimide; DMF, N,N-dimethylformamide; ES-MS, electrospray mass spectrometry; Fmoc, fluorenylmethoxycarbonyl; HOBt, 1-hydroxybenzotriazole; HPLC, high performance liquid chromatography; MBHA, resin p-methylbenzhydrylamine; MeCN, acetonitrile; MeOH, methanol; PAL, 5-(4-aminomethyl-3,5- dimethoxyphenoxy) valeric acid; Palm, palmitoyl; tBu, tert-butyl; THF, tetrahydrofuran; TFA, trifluoroacetic acid; Trt, trityl.

Example 1

Obtaining Ac-βAla-His-Cys-His-OH 5.5 g of Fmoc-L-His(Trt)-OH (8.9 mmol, 1 equiv) dissolved in 55 mL of DCM to which 1.3 mL of DIEA (2.9 mmol, 0.33 equiv) have been added were incorporated to dry 2-chlorotrityl resin (5.5 g, 8.8 mmol). It was left stirring for 5 minutes, after which 2.5 mL of DIEA (5.9 mmol, 0.67 equiv) were added. It was allowed to react for 40 minutes. The remaining chloride groups were blocked by treatment with 4.4 mL of MeOH.

The amino terminal Fmoc group was deprotected as described in general methods and 12.89 g of Fmoc-L-Cys (Trt)-OH (22 mmol, 2.5 equiv) were incorporated to the peptidyl-resin in the presence of DIPCDI (3.39 mL, 22 mmol, 2.5 equiv) and HOBt (3.37 g, 22 mmol, 2.5 equiv) using DMF as a solvent for 1 hour. The resin was subsequently washed as described in general methods and the treatment for deprotecting the Fmoc group was repeated to incorporate the next amino acid. By following the described protocols, 13.63 g of Fmoc-L-His(Trt)-OH (22 mmol, 2.5 equiv) and 6.85 g of Fmoc-βAla-OH (22 mmol, 2.5 equiv) were coupled sequentially with the presence in each coupling of 3.37 g of HOBt (22 mmol, 2.5 equiv) and 3.39 mL of DIPCDI (22 mmol, 2.5 equiv).

The N-terminal Fmoc group was deprotected as described in general methods, the peptidyl-resin was treated for 30 minutes with acetic anhydride (2.1 mL, 22 mmol) in the presence of DIEA (7.53 mL, 22 mmol) using DMF as a solvent, it was washed with DMF (5×1 minutes), DCM (4×1 minutes), diethyl ether (4×1 minutes) and dried under vacuum.

12.36 g of the dry peptidyl-resin was treated with 87 mL of TFA-$^i$Pr$_3$Si—H$_2$O (90:5:5) for 2 hours at room temperature. The filtrates were collected on cold diethyl ether (700 mL), it was filtered through porous plate and the precipitate was washed 5 times with ether (500 mL). The final precipitate was dried under vacuum.

The analysis by HPLC in a gradient from 2 to 32% of MeCN (+0.07% TFA) in H$_2$O (+0.1% TFA) indicated a retention time of 12.63 minutes and a purity greater than 85%. Its molecular weight was determined by ES-MS [(M+H)$^+_{theoretical}$ 509.19, (M+H)$^+_{exp}$ 509.2].

Example 2

Synthesis of Palm-βAla-His-Ser-His-NH$_2$ 0.685 mg of the Fmoc-AM-MBHA resin with a functionalization of 0.73 mmol/g (0.5 mmol) was treated with piperidine-DMF according to the described general protocol for the purpose of eliminating the Fmoc group. 1.58 g of Fmoc-L-His(Trt)-OH (2.5 mmol, 5 equiv) were incorporated to the resin in the presence of DIPCDI (385 μL, 2.5 mmol, 5 equiv) and HOBt (385 mg, 2.5 mmol, 5 equiv) using DMF as a solvent for 1 hour.

The resin was subsequently washed as described in the general methods and the treatment for deprotecting the Fmoc group was repeated to incorporate the next amino acid. By following the described protocols, 0.95 g of Fmoc-L-Ser (tBu)-OH (2.5 mmol, 5 equiv), 1.59 g of Fmoc-L-His(Trt)-OH (2.5 mmol, 5 equiv) and 0.77 g of Fmoc-βAla-OH (2.5 mmol, 5 equiv) were sequentially coupled with the presence in each coupling of 385 mg of HOBt (2.5 mmol, 5 equiv) and 385 μL of DIPCDI (2.5 mmol, 5 equiv).

The N-terminal Fmoc group was deprotected as described in general methods, and 1.28 g of palmitic acid (5 mmol, 10 equiv) pre-dissolved in DMF (10 mL) were incorporated in the presence of 770 mg of HOBt (5 mmol, 10 equiv) and 770 μL of DIPCDI (5 mmol, 10 equiv). It was left reacting for 15 hours, after which the resin was washed with THF (5×1 min), DCM (5×1 min), DMF (5×1 min), MeOH (5×1 min), DMF (5×1 min), THF (5×1 min), DMF (5×1 min), DCM (4×1 min), ether (3×1 min), and was dried under vacuum.

1.17 g of the dry peptidyl-resin were treated with 15 mL of TFA-$^i$Pr$_3$Si—H$_2$O (90:5:5) for 2 hours at room temperature. The filtrates were collected on cold diethyl ether (100 mL), centrifuged for 5 minutes at 4000 rpm and the ether solution was decanted. The washings with ether were repeated 5 times. The final precipitate was dried under vacuum.

The analysis by HPLC in a gradient from 5 to 95% of MeCN (+0.07% TFA) in H$_2$O (+0.1% TFA) showed a retention time of 19.3 minutes and a purity greater than 70%. Its molecular weight was determined by ES-MS [(M+H)$^+_{theoretical}$ 688.45, (M+H)$^+_{exp}$ 688.7].

Example 3

Obtaining Ac-βAla-His-Ser-His-NH—(CH$_2$)$_9$—CH$_3$ 2.0 g of Fmoc-L-His(Trt)-OH (3.23 mmol, 1 equiv) dissolved in 20 mL of DCM to which 500 μL of DIEA (1.1 mmol, 0.33 equiv) have been added were incorporated to dry 2-chlorotrityl resin (2.0 g, 3.3 mmol). It was left stirring for 5 minutes, after which 1 mL of DIEA (2.2 mmol, 0.67 equiv) were added. It was allowed to react for 40 minutes. The remaining chloride groups were blocked by treatment with 1.6 mL of MeOH.

The amino terminal Fmoc group was deprotected on 1 mmol of the aminoacyl-resin as described in general methods and 1.95 g of Fmoc-L-Ser(tBu)-OH (5 mmol, 5 equiv) were incorporated in the presence of DIPCDI (770 μL, 5 mmol, 5 equiv) and HOBt (770 mg, 5 mmol, 5 equiv) using DMF as a solvent for 1 hour. The resin was subsequently washed as described in the general methods and the treatment for deprotecting the Fmoc group was repeated to incorporate the next amino acid. By following the described protocols, 3.09 g of Fmoc-L-His(Trt)-OH (5 mmol, 5 equiv) and 1.60 g of Fmoc-βAla-OH (5 mmol, 5 equiv) were coupled sequentially with the presence in each coupling of 770 mg of HOBt (5 mmol, 5 equiv) and 770 μL of DIPCDI (5 mmol, 5 equiv).

The N-terminal Fmoc group was deprotected as described in general methods, and the peptidyl-resin was treated for 30 minutes with 2.36 mL of acetic anhydride (25 mmol, 25 equiv) in the presence of 4.28 mL of DIEA (25 mmol, 25 equiv) using DMF as a solvent, it was washed with DMF (5×1 minutes), DCM (4×1 minutes), diethyl ether (4×1 minutes) and dried under vacuum.

The completely protected peptide [Ac-βAla-L-His(Trt)-L-Ser(tBu)-L-His(Trt)-OH] was obtained by treatment for 5 minutes of the peptidyl-resin, previously dried under vacuum in the presence of KOH, with a 3% solution of TFA in DCM. The filtrates were collected on cold diethyl ether and the treatment was repeated three times. The ether solutions were rotary evaporated to dryness at room temperature, the precipitate was resuspended in 50% MeCN in H$_2$O and lyophilized. The raw product obtained was analyzed by HPLC in a gradient from 5 to 95% of MeCN (+0.07% TFA) in H$_2$O (+0.1% TFA), showing a retention time of 24.1 minutes and a purity greater than 88%. Its molecular weight was determined by ES-MS [(M+H)$^+_{theoretical}$ 1034.2, (M+H)$^+_{exp}$ 1034.0].

380 mg of Ac-βAla-L-His(Trt)-L-Ser(tBu)-L-His(Trt)-OH (367 μmol) were weighed in a balloon, 350 mg of decylamine (3 equiv) and 30 mL of anhydrous DMF were added. 120 μL of DIPCDI (2 equiv) were added, and it was allowed to react with magnetic stirring at 47° C. The reaction was controlled by means of HPLC by the disappearance of Ac-βAla-L-His(Trt)-L-Ser(tBu)-L-His(Trt)-OH, being completed in 2.5 hours. The solvent was evaporated to dryness and was coevaporated twice with DCM. The obtained residue [Ac-βAla-L-His(Trt)-L-Ser(tBu)-L-His(Trt)-NH—(CH$_2$)$_9$—CH$_3$] was resuspended in 50 mL of a mixture of TFA-DCM-anisole (49:49:2) and was allowed to react for 30 minutes at room temperature. 250 mL of cold diethyl ether was added, the solvent was rotary evaporated and two additional coevaporations were carried out with ether. The residue was dissolved in a 50% mixture of MeCN in H$_2$O and lyophilized.

The analysis by HPLC in a gradient from 5 to 85% of MeCN (+0.07% TFA) in H$_2$O (+0.1% TFA) indicated a retention time of 16.6 minutes and a purity greater than 71%. Its molecular weight was determined by ES-MS [(M+H)$^+_{theoretical}$ 632.4, (M+H)$^+_{exp}$ 632.6].

Example 4

Obtaining Ac-βAla-His-Ser-His-OH

The peptide of Example 4 was obtained by following the same synthetic protocol as in Example 1 (amounts, solvents, excesses and reactants), but incorporating Fmoc-L-Ser(tBu)-OH (8.43 g, 22 mmol) instead of Fmoc-L-Cys(Trt)-OH as the second amino acid. Once the synthesis was completed, the resin was washed with DMF (5×1 minutes), DCM (4×1 minutes), diethyl ether (4×1 minutes) and dried under vacuum.

The peptide was released from the solid support by following the same synthetic protocol as in Example 1 (amounts, solvents, excesses and reactants).

The analysis by HPLC in a gradient from 0 to 10% of MeCN (+0.07% TFA) in H$_2$O (+0.1% TFA) indicated a purity greater than 90% and its molecular weight was determined by ES-MS [(M+H)$^+_{theoretical}$ 493.22, (M+H)$^+_{exp}$ 493.2].

Example 5

Preparation of a Cosmetic Composition Containing Ac-βAla-His-Ser-His-OH

The following formulation was prepared as described in the present invention:

The oils, surfactants and carbomers were weighed in a sufficiently large reactor. The peptide was weighed in another reactor, it was dissolved in water and the preservative (Phenonip®) was added to it. The peptide solution was poured on to the oil solution with constant vigorous stirring. Once the addition is over, the pH is adjusted to 6.5-7.0 with triethanolamine.

| INGREDIENT (INCI Nomenclature) | % BY WEIGHT |
| --- | --- |
| ACRYLATES/C10-30 ALKYL ACRYLATES CROSSPOLYMER | 0.3 |
| CARBOMER | 0.3 |
| C12-15 ALKYL BENZOATE | 17.6 |
| ETHYLHEXYL COCOATE | 2.4 |
| POLYACRYLAMIDE, C13-14 ISOPARAFFIN, LAURETH-7 | 1.0 |
| AQUA (WATER) | q.s.p.100 |
| PHENONIP ® | 0.5 |
| Ac-βAla-His-Ser-His-OH | 0.01 |
| TRIETHANOLAMINE | 0.7 |

Example 6

Preparation of a Cosmetic Composition Containing Ac-βAla-His-Cys-His-OH

The following formulation was prepared as described in the present invention:

The oils, waxes, silicones and carbomers were weighed in a sufficiently large reactor. The mixture is heated to 65-70° C. to melt the waxes. The glycerin was weighed in another reactor, it was resuspended in water and the preservative (Phenonip®) and the triethanolamine were added. The mixture was heated to 65-70° C. with constant vigorous stirring or by means of applying shear force. Once the addition was over, it was allowed to cool with slow stirring and when the mixture is at 40° C., an aqueous Ac-βAla-His-Cys-His-OH solution was added. The cream is allowed to cool to room temperature and the pH is corrected with triethanolamine if necessary.

| INGREDIENT (INCI Nomenclature) | % BY WEIGHT |
| --- | --- |
| MINERAL OIL | 10.0 |
| STEARIC ACID | 3.0 |
| BEESWAX | 2.0 |
| DIMETHICONE | 0.2 |
| CARBOMER | 0.2 |
| GLYCERIN | 3.0 |
| AQUA (WATER) | q.s.p.100 |
| PHENONIP ® | 0.5 |
| Ac-βAla-His-Cys-His-OH | 0.005 |
| TRIETHANOLAMINE | 2.0 |

Example 7

A clinical study of the cosmetic composition described in Example 5 conducted in 20 subjects with bags formed under the eyes showed that the composition can reduce the size of the bags formed under the eyes. The subjects were instructed to apply the cosmetic composition in the eye contour area with a soft massage once a day for two months. Objective measurements of the degree of skin hydration by means of a corneometer (Skinlab®) and of skin elasticity by means of an elastometer were carried out at time 0 and 15, 30 and 60 days after the start of the treatment, and the size of the under-eye bags was also observed by a dermatologist.

The quantification of the results showed a 5.8% increase of the hydration index as well as a 35% increase of the elasticity index after 60 days of treatment. A subjective evaluation by the dermatologist of the appearance of the eye bags according to Friedman's test [Cristoni A. (2001) *La significativitá del risultato sperimentale. Quali test usare? Cosmetic News* 130, January/February pp 30-32] confirmed that 70% of the volunteers experiences a reduction of under-eye bags in only 15 days, which percentage rose to 95% of the volunteers after 60 days of treatment (30% slight reduction, 30% discreet reduction and 35% significant reduction).

According to a first aspect, the present invention relates to a peptide of general formula (I):

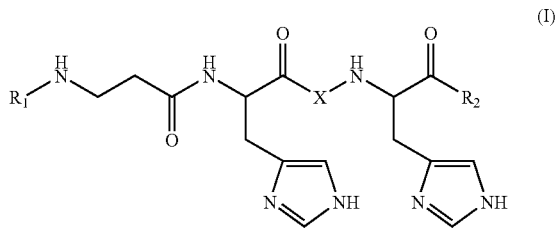

its stereoisomers, its cosmetically and dermopharmaceutically acceptable salts and mixtures thereof, wherein:
X is selected from the group formed by cystenyl, seryl, threonyl and aminobutyryl;
$R_1$ is selected from the group formed by H or alkyl, aryl, aralkyl, and acyl group and,
$R_2$ is selected from the group formed by amino, hydroxy and thiol, substituted or non-substituted with aliphatic or cyclic groups.

According to a second important aspect, in the peptide of general formula (I) $R_1$ is preferably saturated or unsaturated, branched or cyclic, linear $C_2$ to $C_{24}$ acyl.

According to an important aspect of the invention, in the peptide of general formula (I) $R_2$ is preferably amino or hydroxy, substituted or non-substituted with saturated or unsaturated, branched or cyclic, linear aliphatic $C_1$ to $C_{24}$ groups.

According to an important aspect of the invention, in the peptide of general formula (I) X is preferably L-seryl, $R_1$ is H and $R_2$ is amino, substituted or non-substituted with methyl or ethyl or dodecyl or hexadecyl groups.

According to an important aspect of the invention, in the peptide of general formula (I) X is preferably L-seryl, $R_1$ is acetyl and $R_2$ is amino, substituted or non-substituted with methyl or ethyl or dodecyl or hexadecyl groups.

According to an important aspect of the invention, in the peptide of general formula (I) X is preferably L-seryl, $R_1$ is palmitoyl and $R_2$ is amino, substituted or non-substituted with methyl or ethyl or dodecyl or hexadecyl groups.

According to an important aspect of the invention, in the peptide of general formula (I) X is preferably L-seryl, $R_1$ is H and $R_2$ is hydroxy, substituted or non-substituted with methyl or ethyl or dodecyl or hexadecyl groups.

According to an important aspect of the invention, in the peptide of general formula (I) X is preferably L-seryl, $R_1$ is acetyl and $R_2$ is hydroxy, substituted or non-substituted with methyl or ethyl or dodecyl or hexadecyl groups.

According to an important aspect of the invention, in the peptide of general formula (I) X is preferably L-seryl, $R_1$ is palmitoyl and $R_2$ is hydroxy, substituted or non-substituted with methyl or ethyl or dodecyl or hexadecyl groups.

According to another important aspect, the present invention relates to a process for obtaining a peptide of general formula (I) based on solid-phase peptide synthesis.

According to another important aspect, the present invention relates to a process for obtaining a peptide of general formula (I) using protective groups selected from the group formed by Fmoc/tButyl, Fmoc/trityl and Fmoc/allyl.

According to another important aspect, the present invention relates to a cosmetic or dermopharmaceutical composition comprising a cosmetically or dermopharmaceutically effective amount of at least one peptide of formula (I) and at least one cosmetically or demopharmaceutically acceptable excipient or adjuvant.

According to another important aspect, the present invention relates to a cosmetic or dermopharmaceutical composition containing a peptide of general formula (I) incorporated to a cosmetically or demopharmaceutically acceptable carrier selected from the group formed by liposomes, millicapsules, microcapsules and nanocapsules, sponges, millispheres, microspheres, nanospheres, milliparticles, microparticles and nanoparticles.

According to another important aspect, the present invention relates to a cosmetic or dermopharmaceutical composition having a formulation selected from the group formed by oil-in-water emulsions, water-in oil emulsions, creams, milks, lotions, gels, ointments, liniments, serums, mousses, balms, foams, body oils, soaps, bars, pencils and sprays.

According to another important aspect, the present invention relates to a cosmetic or dermopharmaceutical composition containing a peptide of general formula (I) incorporated to solid supports selected from the group formed by towelettes, hydrogels, patches and face masks.

According to another important aspect, the present invention relates to a cosmetic or dermopharmaceutical composition containing a peptide of general formula (I) incorporated to make-up line products selected from the group formed by concealers, make-up foundations, lotions, and make-up removal lotions.

According to another important aspect, the present invention relates to the use of a peptide of formula (I) in the manufacture of a cosmetic or dermopharmaceutical composition for the treatment of skin.

According to another important aspect, the present invention relates to the use of a peptide of formula (I) in the manufacture of a cosmetic or dermopharmaceutical composition for the treatment of facial skin.

According to another important aspect, the present invention relates to the use of a peptide of formula (I) in the manufacture of a cosmetic or dermopharmaceutical composition for reducing or removing bags formed under the lower eye contour.

The invention claimed is:
1. A peptide of general formula (I):

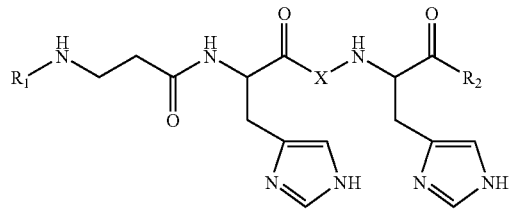

its stereoisomers, mixtures thereof, and its cosmetically and dermopharmaceutically acceptable salts, wherein:
X is selected from the group formed by cystenyl, seryl, threonyl and aminobutyryl;
$R_1$ is selected from the group formed by H or alkyl, aryl, aralkyl and acyl group;
and $R_2$ is selected from the group formed by amino, hydroxy and thiol, substituted or non-substituted with aliphatic or cyclic groups.

2. A peptide according to claim 1, wherein $R_1$ is saturated or unsaturated, branched or cyclic, linear $C_2$ to $C_{24}$ acyl.

3. A peptide according to claim 1, wherein $R_2$ is amino or hydroxy, substituted or non-substituted with saturated or unsaturated, branched or cyclic, linear $C_1$ to $C_{24}$ aliphatic groups.

4. A peptide according to claim 1, wherein X is L-Ser, $R_1$ is H and $R_2$ is amino, substituted or non-substituted with methyl or ethyl or dodecyl or hexadecyl groups.

5. A peptide according to claim 1, wherein X is L-Ser, $R_1$ is acetyl and $R_2$ is amino, substituted or non-substituted with methyl or ethyl or dodecyl or hexadecyl groups.

6. A peptide according to claim 1, wherein X is L-Ser, $R_1$ is palmitoyl and $R_2$ is amino, substituted or non-substituted with methyl or ethyl or dodecyl or hexadecyl groups.

7. A peptide according to claim 1, wherein X is L-Ser, $R_1$ is H and $R_2$ is hydroxy, substituted or non-substituted with methyl or ethyl or dodecyl or hexadecyl groups.

8. A peptide according to claim 1, wherein X is L-Ser, $R_1$ is acetyl and $R_2$ is hydroxy, substituted or non-substituted with methyl or ethyl or dodecyl or hexadecyl groups.

9. A peptide according to claim 1, wherein X is L-Ser, $R_1$ is palmitoyl and $R_2$ is hydroxy, substituted or non-substituted with methyl or ethyl or dodecyl or hexadecyl groups.

10. A cosmetic or dermopharmaceutical composition comprising a cosmetically or demopharmaceutically acceptable excipient or adjuvant; and
    an effective amount of the peptide claim 1.

11. A cosmetic or dermopharmaceutical composition according to claim 10, wherein contains at least one peptide of general formula (I) incorporated to a cosmetically or demopharmaceutically acceptable carrier selected from the group formed by liposomes, millicapsules, microcapsules, nanocapsules, sponges, millispheres, microspheres, nanospheres, milliparticles, microparticles and nanoparticles.

12. A cosmetic or dermopharmaceutical composition according to claim 10, wherein it has a formulation selected from the group formed by oil-in-water emulsions, water-in-oil emulsions, milks, lotions, gels, ointments, balms, foams, body oils, soaps, bars, pencils, sprays, creams, liniments, unguents, serums and mousses.

13. A cosmetic or dermopharmaceutical composition according to claim 10, wherein it contains at least one peptide of general formula (I) incorporated to solid supports selected from the group formed by towelletes, hydrogels, patches and face masks.

14. A cosmetic or dermopharmaceutical composition according to claim 10, wherein it contains at least one peptide of general formula (I) incorporated to make-up line products selected from the group formed by concealers, make-up foundations, lotions, and make-up removal lotions.

15. A method of treating facial skin in need skin, comprising administering to the skin an effective amount of a peptide of claim 1 for reducing bags formed under the lower eye contour.

16. The method of claim 15, wherein a cosmetic or dermopharmaceutical composition comprises the peptide of general formula (I).

17. A peptide of general formula (I):

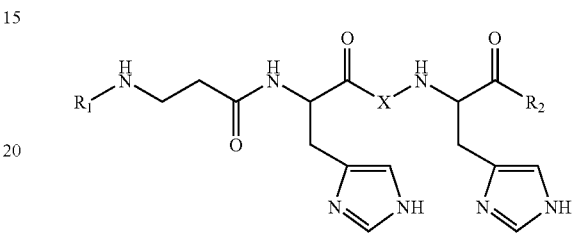

its stereoisomers, mixtures thereof, and its cosmetically and dermopharmaceutically acceptable salts, wherein:

X is selected from the group formed by cystenyl, seryl, threonyl and aminobutyryl;

$R_1$ is selected from the group formed by H or saturated or unsaturated, branched or cyclic, linear $C_2$ to $C_{24}$acyl;

and $R_2$ is selected from the group formed by amino, hydroxy and thiol, substituted or non-substituted with aliphatic or cyclic groups.

18. A cosmetic or dermopharmaceutical composition, comprising a cosmetically or demopharmaceutically acceptable excipient or adjuvant; and
    an effective amount of the peptide claim 17.

19. A method of treating facial skin in need skin, comprising administering to the skin an effective amount of the peptide of claim 17 for reducing bags formed under the lower eye contour.

\* \* \* \* \*